US00PP20535P2

(12) United States Plant Patent
Perkins

(10) Patent No.: US PP20,535 P2
(45) Date of Patent: Dec. 8, 2009

(54) ***ANGELONIA* PLANT NAMED 'CAR PINK09'**

(50) Latin Name: *Angelonia angustifolia*
Varietal Denomination: Car Pink09

(75) Inventor: Ralph T. Perkins, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/313,053

(22) Filed: Nov. 17, 2008

(51) Int. Cl.
*A01H 5/00* (2006.01)

(52) U.S. Cl. ..... Plt./404

(58) Field of Classification Search ..... Plt./404
See application file for complete search history.

*Primary Examiner*—Kent L Bell
(74) *Attorney, Agent, or Firm*—S. Matthew Edwards

(57) ABSTRACT

A new *Angelonia* plant named 'Car Pink09', particularly distinguished by the light red-purple flower color, upright habit, dense foliage, strong stems, and good floriferousness.

1 Drawing Sheet

Latin name of the genus and species of the plant claimed: *Angelonia angustifolia.*

Varietal denomination: 'Car Pink09'.

BACKGROUND OF THE NEW PLANT

The present invention comprises a new *Angelonia,* botanically known as *Angelonia angustifolia,* and hereinafter referred to by the variety name 'Car Pink09'.

'Car Pink09' is a product of a planned breeding program. The new cultivar 'Car Pink09' has light red-purple flower color, more upright habit, with dense foliage, strong stems, and good floriferousness.

'Car Pink09' originated from a hybridization in a controlled breeding program in Gilroy, Calif. U.S.A. The female parent was an unpatented hybrid identified as '216-4' with pink color. '216-4' has a darker pink color, a less compact habit, and has fewer and larger flowers than 'Car Witti09'.

The male parent of 'Car Pink09' was an unpatented hybrid seedling identified as '144-1' with light pink color. '144-1' has a less compact habit, fewer branches and larger foliage, and fewer but larger flowers than 'Car Pink09'.

'Car Pink09' was selected as one flowering plant within the progeny of the stated cross in July 2003 in a controlled environment in Gilroy, Calif. U.S.A. The pollination was made in October 2002 and the seed sowing was completed in April 2003.

The first act of asexual reproduction of 'Car Pink09' was accomplished using vegetative cuttings from the initial selection in July 2003 in a controlled environment in Gilroy, Calif. U.S.A.

Horticultural examination of plants grown from cuttings of the plant initiated in July 2003 in Gilroy, Calif. U.S.A., and continuing thereafter, has demonstrated that the combination of characteristics as herein disclosed for 'Car Pink09' are firmly fixed and are retained through successive generations of asexual reproduction.

'Car Pink09' has not been observed under all possible environmental conditions. The phenotype may vary significantly with variations in environment such as temperature, light intensity and day length.

A Plant Breeder's Right for this cultivar was applied for in Canada on Dec. 24, 2007. 'Car Pink09' has not been made publicly available more than one year prior to the filing of this application.

DESCRIPTION OF THE DRAWINGS

The accompanying photographic drawing shows typical flower and foliage characteristics of 'Car Pink09' with colors being as true as possible with an illustration of this type. The photographic drawing shows a flowering potted plant of the new variety and a close-up of the flowers. The plant was grown and photographed in Gilroy Calif. U.S.A. in July 2008 and was about 5 months old.

DETAILED BOTANICAL DESCRIPTION

The measurements were taken in Gilroy, Calif. U.S.A. in October 2008 on plants that were growing in 6 inch pots in a greenhouse. Culture of these plants started in March. The plants were about 6–7 months old.

Color Chart used: Royal Horticultural Society Colour Chart (R.H.S.) 2001

BRIEF SUMMARY OF INVENTION

The following observations, measurements, and comparisons describe plants grown in Gilroy, Calif. U.S.A. The following traits have been repeatedly observed and are determined to be basic characteristics of the new variety. The combination of these characteristics distinguishes this *Angelonia* as a new and distinct variety.

TABLE 1

DIFFERENCES BETWEEN THE NEW VARIETY 'CAR PINK09' AND A SIMILAR VARIETY

| | 'Car Pink09' | 'Balangpili' |
|---|---|---|
| Flower size | Larger | Smaller |
| Plant habit | More upright | Less upright and is broader |
| Foliage color | Darker green | Lighter green |

Plant:
*Form, growth and habit.*—Upright and relatively narrow habit, dense foliage, strong stems.
*Plant height.*—35–42 cm.
*Plant height (inflorescence included).*—50–58 cm.
*Plant width.*—35–44 cm.

Foliage:
*Immature, leaf color, upper surface.*—RHS 138A.
*Lower surface.*—RHS 138B.
*Mature, leaf color, upper surface.*—RHS 147A.
*Lower surface.*—RHS 138A.
*Length.*—6.5–7.5 cm.
*Width.*—1.1–1.3 cm.
*Shape.*—Elliptical.
*Base shape.*—Cuneate.
*Apex shape.*—Acute.
*Margin.*—Serrate.
*Texture.*—Glabrous.
*Color of veins, upper surface.*—RHS 144C.
*Color of veins, lower surface.*—RHS 144C.

Stem:
*Number of main stems per plant.*—5–8.
*Number of leaves per stem (before it branches).*—10–15.
*Color of stem.*—RHS 144A.
*Length of stem.*—25–30 cm.
*Diameter.*—0.3 cm.
*Length of internodes.*—2–4 cm.
*Texture.*—Glabrous.

Inflorescence:
*Type.*—Terminal raceme; florets solitary in leaf axis.
*Number of florets per raceme.*—25–30.
*Raceme length.*—14–19 cm.
*Color of pedicel.*—RHS 144A base color; anthocyanin overlay of RHS 183B.
*Length of pedicel.*—1.5–1.6 cm.
*Diameter of pedicel.*—0.05 cm.
*Texture.*—Glandular hairs.
*Duration of flowering.*—Continuous flowering throughout the summer.
*Lastingness of flowers.*—About 6–7 days.
*Fragrance.*—None.

Corolla:
*Form.*—Single; 5-petaled, fused at base.
*Length of floret.*—2.4–2.5 cm.
*Width of floret.*—2.2–2.4 cm.
*Color upper petals, upper surface.*—RHS 65B.
*Color upper petals, lower surface.*—RHS 65B.
*Size upper lip petal length.*—0.6–0.7 cm from corolla opening.
*Size upper lip petal width.*—0.8–0.9 cm.
*Color lower lip, lateral petals, upper surface.*—RHS 65C but lighter in patches.
*Color lower lip, lateral petals, lower surface.*—RHS 65C but softer.
*Size lower lip, lateral petals length.*—0.8–1.0 cm from corolla opening.
*Size lower lip, lateral petals width.*—0.9–1.0 cm.
*Color lower lip, mid- petal, upper surface.*—RHS 65C base color; RHS 65B margins; RHS 65D basally; RHS 61A very small spots.
*Color lower lip, mid- petal, lower surface.*—RHS 65C but softer.
*Size lower lip, mid- petal length.*—1.0–1.1 cm from corolla opening.
*Size lower lip, mid- petal width.*—0.9–1.0 cm.
*Petal shape.*—Obovate.
*Apex shape.*—Rounded.
*Margin.*—Entire.
*Petal texture.*—Papillose and a few glandular hairs along the corolla opening.
*Corolla color, inside.*—RHS N155B base color; RHS 65B basally; RHS 61A spots; RHS 144A at base of filaments.
*Corolla color, outside.*—RHS 65C.

Bud (just before opening):
*Color.*—RHS 155A to RHS 157C on the underside; RHS 56B with RHS 55B mottled overlay on the upper side.
*Length.*—1.0–1.3 cm.
*Width.*—0.7–1.0 cm.
*Shape.*—Ovate.

Calyx:
*Number of sepals.*—5 fused at base.
*Color of sepals.*—Both surfaces: RHS 147B base color; overlaid lightly with RHS N186C.
*Length of sepals.*—0.3–0.4 cm.
*Width of sepals.*—0.1–0.15 cm.
*Sepal shape.*—Lanceolate.
*Apex shape.*—Acute.
*Margins.*—Entire.
Texture.—Mostly glabrous, but has a few glandular hairs.

Reproductive organs:
*Pistil.*—1.
*Length.*—0.3–0.35 cm.
*Style color.*—RHS N155B but whiter.
*Style length.*—0.1–0.15 cm.
*Stigma color.*—RHS N155B but whiter.
*Number of stamens.*—4, in pairs.
*Color of filaments.*—RHS N155B.
*Length filaments.*—0.4–0.5 cm.
*Color of pollen.*—RHS 155B.
*Pollen amount.*—Scarce.
*Fertility/seed set.*—Not observed on this hybrid.

Disease/pest resistance: Disease resistance or susceptibility has not been observed on this hybrid.

What is claimed is:

1. A new and distinct variety of *Angelonia* plant named 'Car Pink09', substantially as illustrated and described herein.

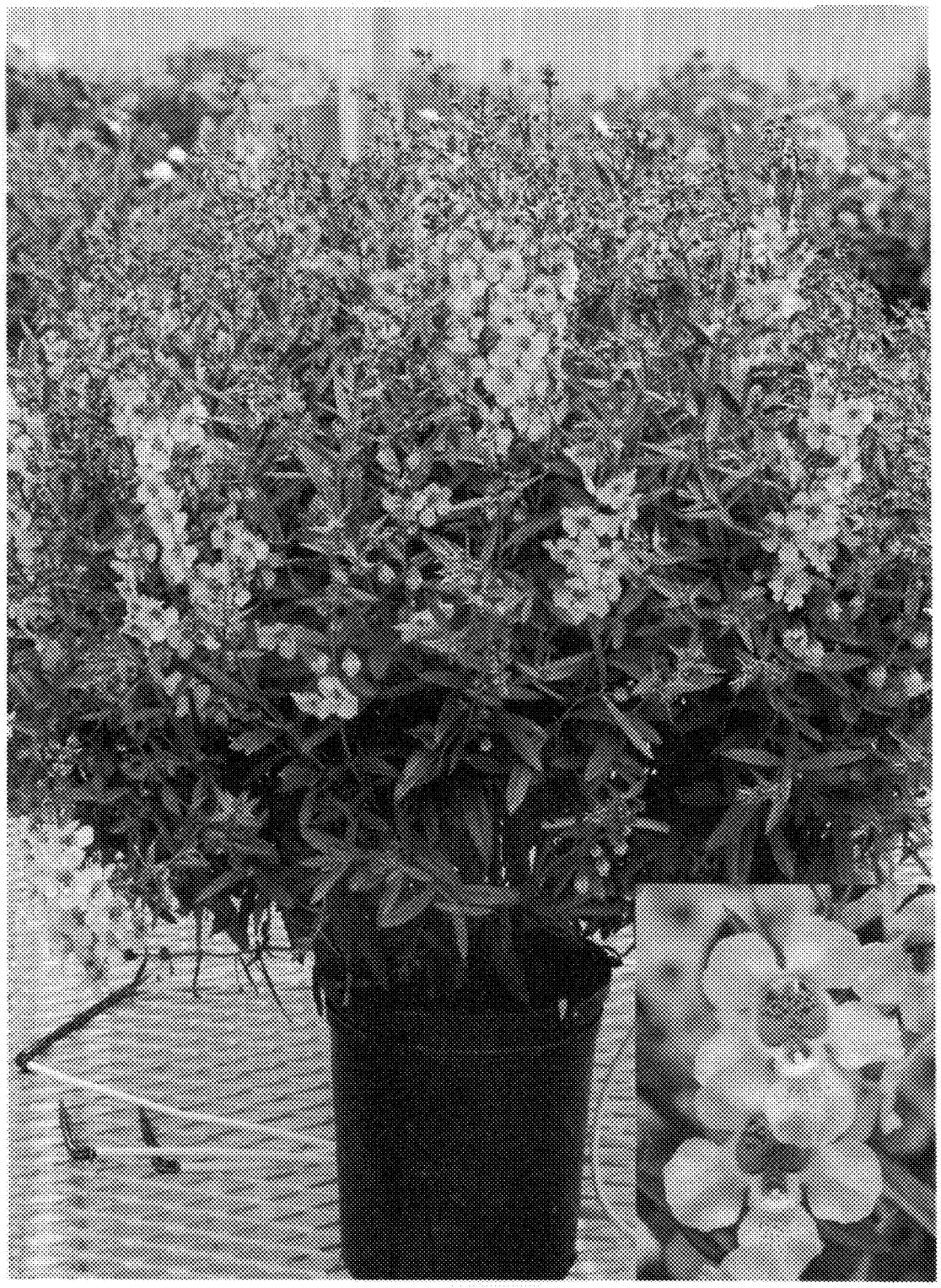

* * * * *